(12) United States Patent
Crumpton et al.

(10) Patent No.: US 8,485,036 B2
(45) Date of Patent: Jul. 16, 2013

(54) CIRCUMFERENTIAL WELD SCANNER WITH AXIAL DRIFT PREVENTION

(75) Inventors: Thomas H. Crumpton, Wilmington, NC (US); Edmund S. Mercier, Wilmington, NC (US)

(73) Assignee: GE-Hitachi Nuclear Energy Americas LLC, Wilmington, NC (US)

(*) Notice: Subject to any disclaimer, the term of this patent is extended or adjusted under 35 U.S.C. 154(b) by 314 days.

(21) Appl. No.: 13/026,908

(22) Filed: Feb. 14, 2011

(65) Prior Publication Data
US 2012/0204645 A1 Aug. 16, 2012

(51) Int. Cl.
*G01N 29/265* (2006.01)

(52) U.S. Cl.
USPC .............................................. 73/637; 73/622

(58) Field of Classification Search
USPC .............................. 73/622, 637; 376/245, 249
See application file for complete search history.

(56) References Cited

U.S. PATENT DOCUMENTS

| | | | |
|---|---|---|---|
| 3,934,457 A * | 1/1976 | Clark et al. | 73/637 |
| 4,387,598 A * | 6/1983 | Jamieson et al. | 73/637 |
| 5,007,291 A | 4/1991 | Walters et al. | |
| 6,745,136 B2 | 6/2004 | Lam et al. | |
| 7,412,890 B1 | 8/2008 | Johnson et al. | |
| 7,694,569 B2 | 4/2010 | McGrath et al. | |
| 2009/0314089 A1 | 12/2009 | Brignac et al. | |

* cited by examiner

*Primary Examiner* — John Chapman, Jr.
(74) *Attorney, Agent, or Firm* — Parks IP Law LLC; Cynthia R. Parks, Esq.

(57) ABSTRACT

Inspection of circumferential sections of pipe or other conduit using an ultrasonic scanning apparatus is provided, wherein axial drift of the ultrasonic scanning apparatus is prevented using a guide track assembly. The guide track assembly is rigidly coupled to the ultrasonic scanning apparatus in the axial direction, but allows rotational motion of the ultrasonic scanning apparatus directly along the outer surface of the conduit using a drive chain that is driven by a circumferential drive. Secure rotational motion without drift between the guide track assembly and the ultrasonic scanning apparatus is maintained by the rigid coupling and by a spring-loaded wheel housing assembly that maintains contact of wheels that travel along the guide track. The ultrasonic scanning apparatus includes a transducer with spring-loaded gimbaling that maintains optimal proximity with the conduit surface. The transducer is translated axially along linear journals that extend along the conduit with a linear actuator.

20 Claims, 4 Drawing Sheets

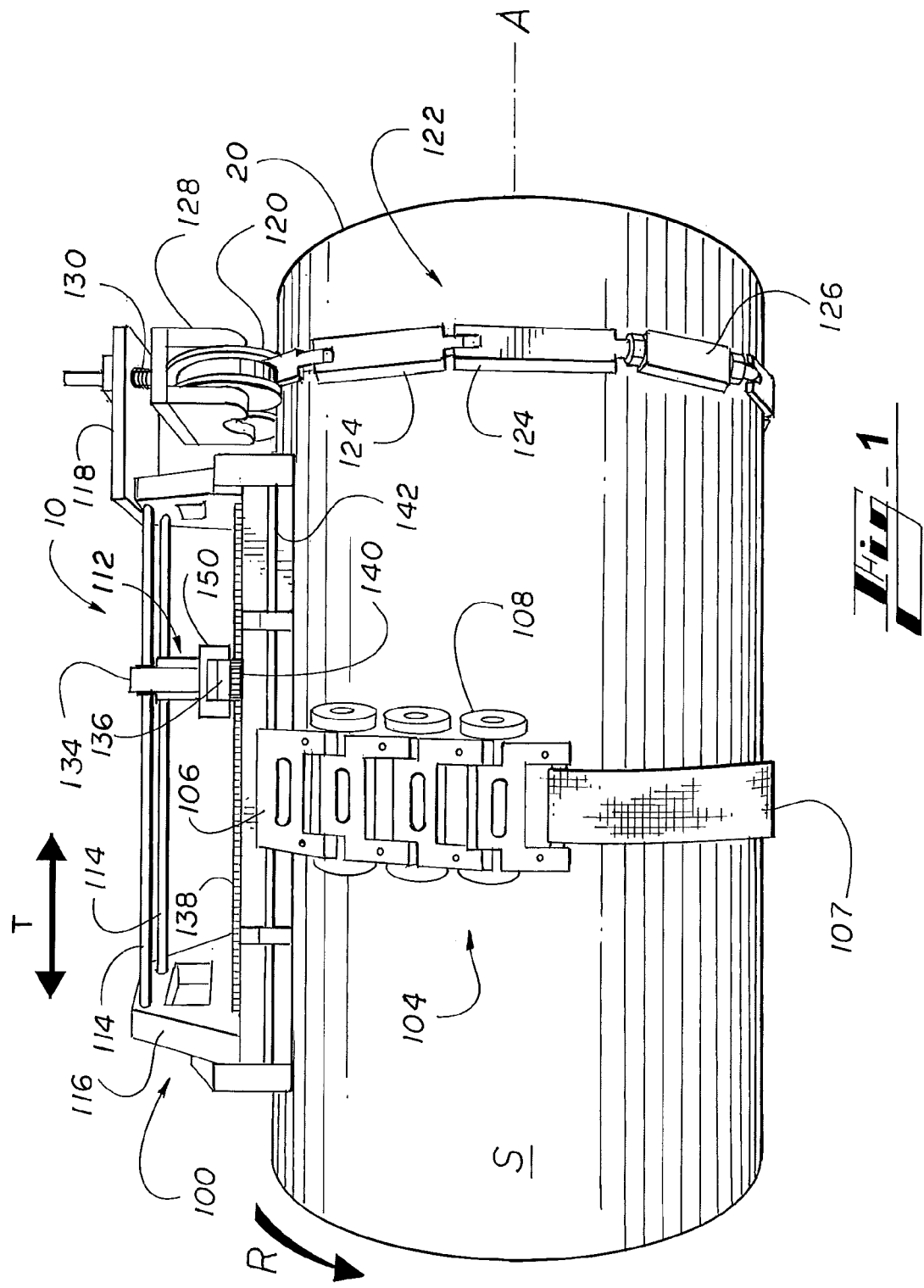
Fig_1

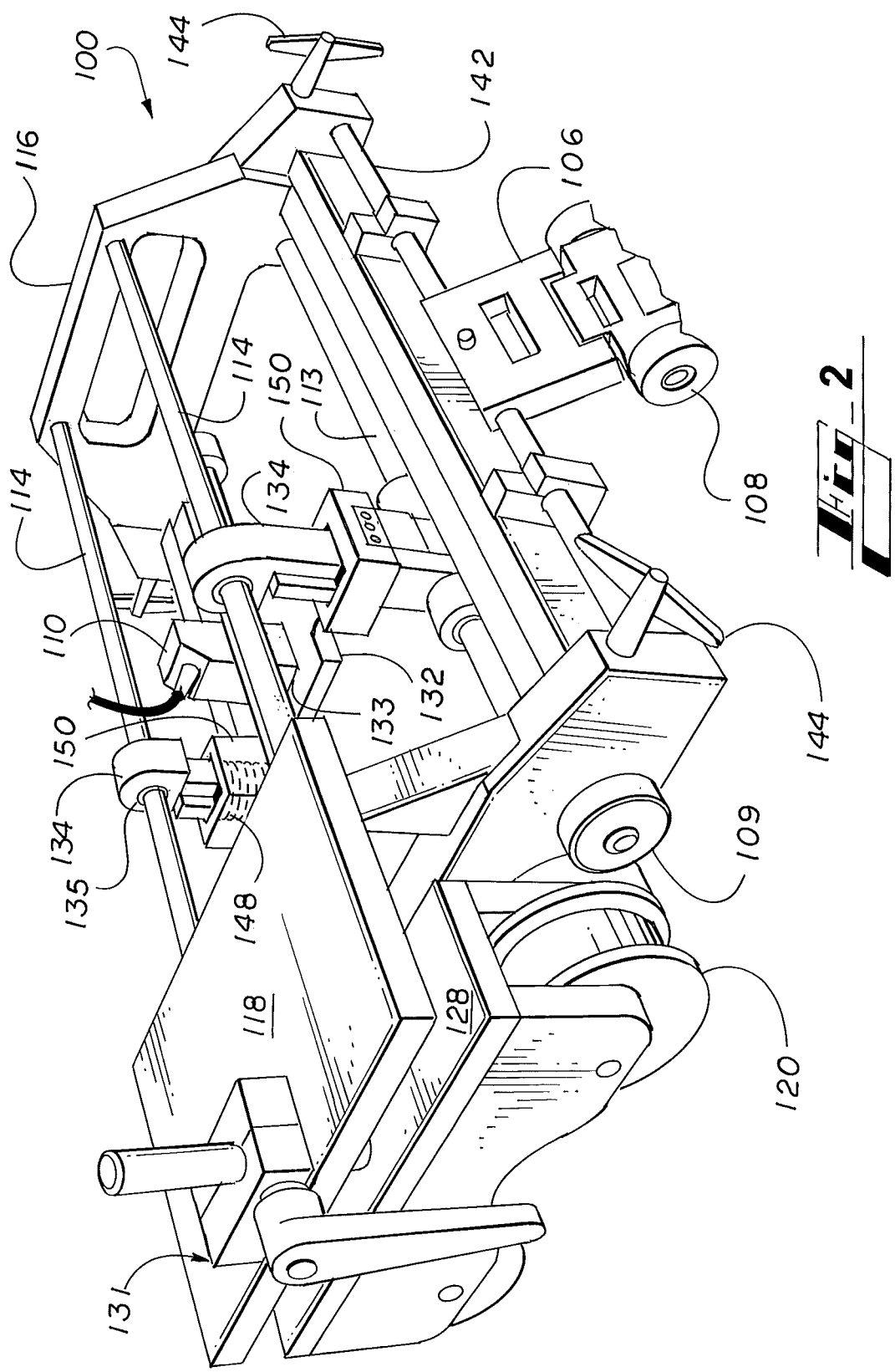
Fig_2

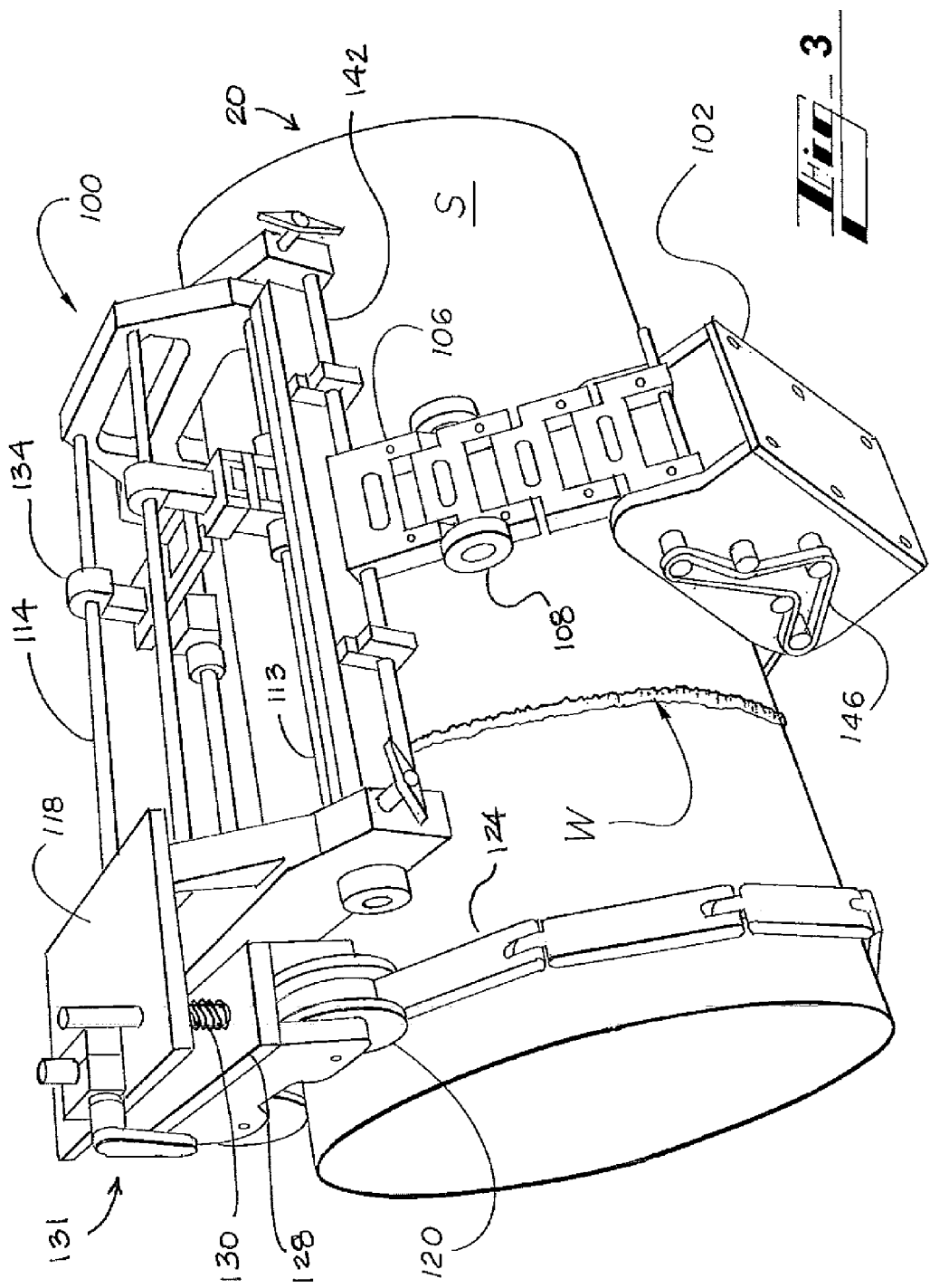

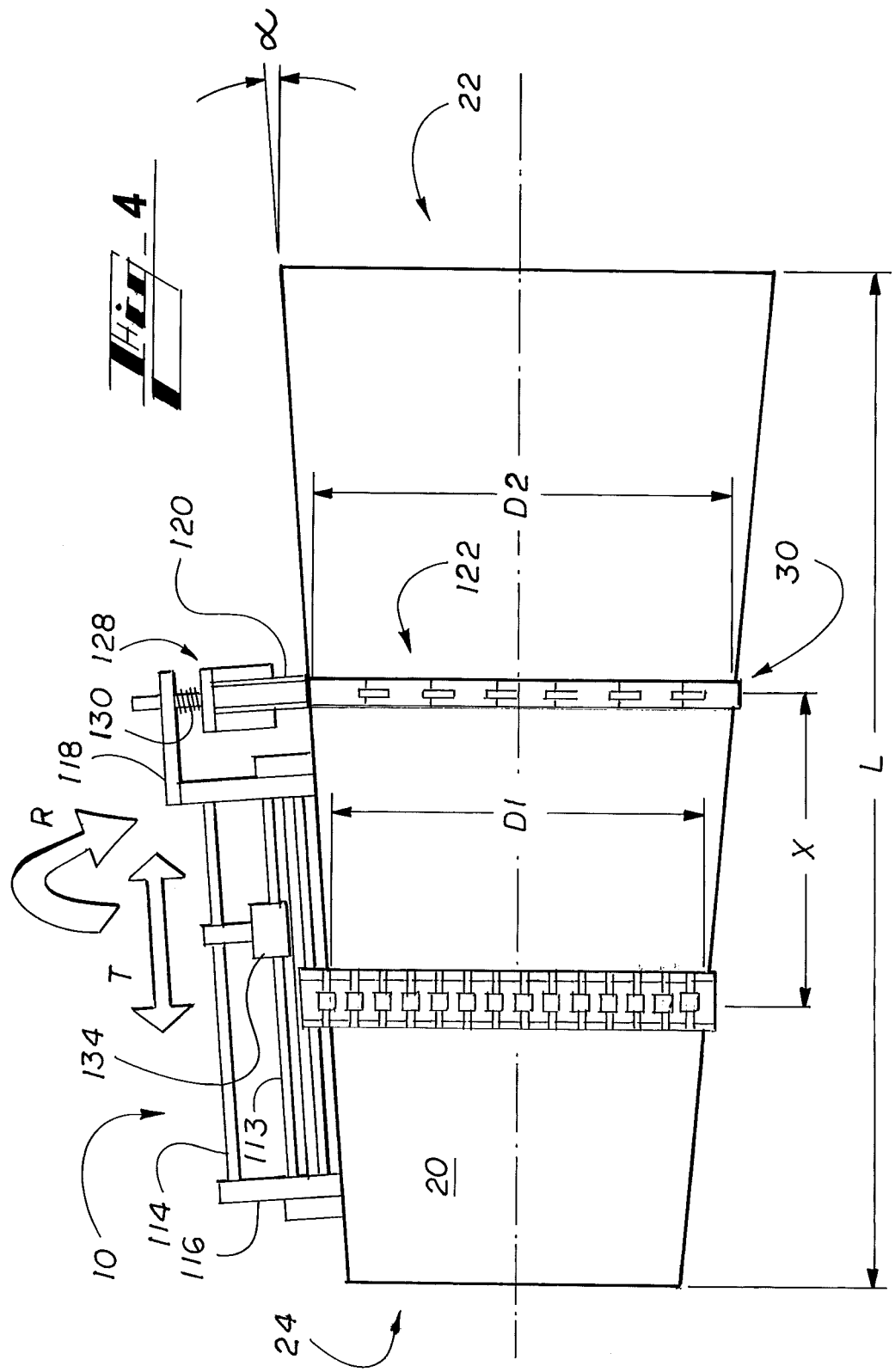

CIRCUMFERENTIAL WELD SCANNER WITH AXIAL DRIFT PREVENTION

TECHNICAL FIELD

The present invention relates generally to nuclear reactors, and more particularly, to devices for inspection of circumferential welds within a nuclear reactor pressure vessel.

BACKGROUND OF THE INVENTION

Typical protocols call for inspection of welds within a nuclear reactor during scheduled outages. Inspection devices are used to scan the welds to detect intergranular stress corrosion cracking (IGSCC), which has been known to occur for example, in connection with primary system piping dissimilar metal (DM) welds.

Circumferential welds extend around the periphery of cylindrical conduits, such as the pipes and tubes commonly found in a reactor system. These welds may be inspected by positioning a scanning apparatus proximate to an outer surface of a pipe adjacent to the location of a weld, and rotating the scanning apparatus about the circumference of the pipe to inspect the entire extent of the weld. The inspection cannot be thorough and precise if the apparatus drifts axially so as to uncontrollably spiral or shift as it rotates around the pipe. In fact, even if the scanning apparatus is designed to follow a helical path, axial drift significantly increases the risk of missing defects in regions that escape inspection.

Previous attempts to address the problem include systems that detect drift and correcting axial alignment reactively by steering the instrument to compensate for detected drift. However, detection of drift necessarily means that the drift has occurred, so the resulting inaccuracy has already impacted the precision of the inspection. Other attempts to prevent drift involve driving the scanning apparatus along an external track that is substantially fixedly mounted around the circumference of the conduit. Wheels and gears engage the external track such that the scanner rides on the external track rather than on the surface of the conduit. However, riding above the surface of the conduit on the external track elevates the profile of the scanning apparatus, which limits its ability to operate in areas with limited clearance. To achieve axial translation, the transducer element of the scanning apparatus typically articulates axially along an extension arm that extends away from the external track. An extended arm often fails to maintain stable and consistent contact or proximity between the scanning apparatus and the conduit, particularly when scanning the underside of a conduit, which results in hysteresis.

Achieving the desired level of precision is especially difficult when inspecting a tapered pipe that has diameters that vary along its length, or when using the same apparatus to inspect different various diameter pipes. There is a need, therefore, for systems and methods that prevent axial drift, and that are usable with various sized conduit and as well as with tapered conduit.

BRIEF DESCRIPTION OF THE INVENTION

The various embodiments of the present invention address the shortcomings of the prior art with a circumferential weld inspection scanner with axial drift prevention means. Among many advantages, the circumferential weld inspection scanner is particularly useful with tapered pipes or other conduit, as it features a drive chain assembly that is spaced apart from a guide track assembly, and a carriage that extends therebetween. The guide track assembly prevents axial drift by securing axial alignment of a circumferential weld scanning instrument, such as but not limited to, a dissimilar metal phased array (DMPA) pipe scanner, although use in connection with other nondestructive inspection instruments are contemplated.

More specifically, one embodiment is a guide track assembly for preventing axial drift of an ultrasonic scanning apparatus that is mounted directly on a circumferential section of conduit. The guide track assembly that includes a guide track that is configured to be fixedly secured adjacent to a circumferential section of a cylindrical conduit (such as, the section near the weld at the nozzle end of a reactor pipe) and a coupling for rotatably engaging the ultrasonic scanner with the guide track. As used herein, the term "cylindrical" means substantially cylindrical—that is, resembling a cylinder having a single curved side wall and a substantially circular or elliptical cross-section. The term "conduit" refers to a substantially cylindrical and hollow structure (such as a pipe or tube) for carrying water, steam or other fluids. The guide track mounts directly to surface of the cylindrical conduit, and the guide track assembly further includes a coupling for defining a substantially axially rigid connection between the ultrasonic scanning apparatus and the guide track. The guide track is configured to be spaced apart from the ultrasonic scanning apparatus, such that the ultrasonic scanning apparatus can rotate directly on the surface of the conduit without experiencing axial drift. To this end, the coupling including at least one wheel that straddles the track to maintain alignment of the ultrasonic scanning apparatus. In certain of the various embodiments, a spring-loaded junction is connected to the coupling, the spring-loaded junction generating a downward force on the wheel to maintain contact with the guide track. Although this spring-loaded junction is optional, it is particularly useful as used with tapered conduits.

Another embodiment is an ultrasonic scanning assembly for inspecting a circumferential weld joining sections of a pipe. The ultrasonic scanning assembly includes a carriage that can rotate around the pipe and that supports a transducer that can translate along journals to access at least a portion of the length of the pipe, such that the ultrasonic scanning assembly can inspect the entirety of a section of pipe, and particularly, the regions adjacent to and including a circumferential weld. The ultrasonic scanning assembly includes at least one elongated journal for providing translational motion to a transducer configured to travel axially along the arm. The transducer is mounted within a housing that engages the journal and can be driven along the journal. The transducer gimbaling is spring-loaded, so that the desired contact or close proximity between the transducer and the conduit surface is consistently maintained.

The ultrasonic scanning assembly further includes a circumferential drive configured to generate rotational motion of the carriage, a drive chain configured to hold the carriage in close association to the pipe and translate to the carriage rotational motion generated by the circumferential drive, a guide track that is configured to be fixedly secured adjacent to the circumferential weld and a coupling for defining a substantially axially rigid connection between the carriage and the guide track. A drive chain extends around the conduit and configured to hold the carriage in close association to the conduit and to translate to the carriage rotational motion generated by the circumferential drive.

Yet another embodiment is method for preventing axial drift while inspecting a circumferential weld in a cylindrical conduit using an ultrasonic scanner. The method includes fixedly extending a guide track around the conduit adjacent to the weld, rotatably mounting the ultrasonic scanning apparatus to the surface of the conduit and coupling the guide track and the ultrasonic scanning apparatus such that the guide track is configured to limit axial displacement of the ultrasonic scanning apparatus during rotation of the ultrasonic scanning apparatus around the conduit.

The foregoing has broadly outlined some of the aspects and features of the various embodiments, which should be construed to be merely illustrative of various potential applications. Other beneficial results can be obtained by applying the disclosed information in a different manner or by combining various aspects of the disclosed embodiments. Other aspects and a more comprehensive understanding may be obtained by referring to the detailed description of the exemplary embodiments taken in conjunction with the accompanying drawings, in addition to the scope defined by the claims.

BRIEF DESCRIPTION OF DRAWINGS

FIG. 1 is a front elevational view of an ultrasonic scanning apparatus for inspecting a circumferential weld in accordance with one embodiment of the invention, showing a guide track assembly maintaining axial alignment with respect to an exemplary conduit.

FIG. 2 is a more detailed partial perspective view showing a carriage component and transducer element of the ultrasonic scanning apparatus of FIG. 1.

FIG. 3 is a rear perspective view of the ultrasonic scanning apparatus of FIG. 1, showing an exemplary circumferential drive assembly.

FIG. 4 is a diagram showing an embodiment of the ultrasonic scanning apparatus as used to inspect an exemplary tapered conduit.

DETAILED DESCRIPTION OF THE INVENTION

As required, detailed embodiments are disclosed herein. It must be understood that the disclosed embodiments are merely exemplary of and may be embodied in various and alternative forms, and combinations thereof. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

An exemplary environment for implementing the various embodiments of the present invention is a boiling water reactor (BWR) core. In the description that follows, the various embodiments are described in the context of an ultrasonic scanning apparatus that includes a circumferential weld scanner, such as a dissimilar metal phased array (DMPA) pipe scanner. Those skilled in the art will readily appreciate that any number of other rotatable scanning instruments for inspecting circumferential sections of conduit will benefit from secure axial alignment, so neither the specific reactor conduit nor the particular weld scanner described is intended to limit the scope of the invention.

Referring now to FIGS. 1-3, the exemplary ultrasonic scanning apparatus 10, an ultrasonic instrument such as a dissimilar metal phased array (DMPA) pipe scanner, includes a carriage 100 and a circumferential drive 102. The carriage 100 is connected to the circumferential drive 102 via a drive chain 104, which includes a series of links 106 and rollers 108. With particular reference to FIGS. 1 and 3, the circumferential drive 102 provides rotational motion R of the carriage 100 by driving the drive chain 104 to which the carriage 100 is engaged. Axial translation T of a transducer 110 mounted on the carriage 100 is provided by an axial drive 112 and along one or more linear journals 113, 114 via any suitable mechanical or electromechanical mechanism, such as a linear actuator. The linear journals 113, 114 are elongated shafts that extend between opposite ends of a frame 116 component of the carriage 100.

In practice, the various embodiments of the ultrasonic scanning apparatus 10 can be deployed when a reactor is shut down, and certain conduits 20 in the drywell of a reactor are inspected in their in service positions. The ultrasonic scanning apparatus 10 can be installed on conduits 20 that are disposed horizontally, vertically, or at an angle. Based on access studies that describe the number and characteristics of welds W (FIG. 3) and other circumferential sections that are to be inspected, technicians pre-build an ultrasonic scanning apparatus 10 for the particular task. Pre-building the ultrasonic scanning apparatus 10 includes sizing its guide chain 122 and drive chain 104 to provide secure rotation around the conduit 20 during the inspection, as well as determining the desired orientation and positioning for installation of the ultrasonic scanning apparatus 10. The ultrasonic scanning apparatus 10 may be installed such that its carriage 100 is adjacent to a weld W and its transducer 100 can access the weld W and adjacent areas by translating along the journals 113, 114 and around the conduit 20 as driven by the circumferential drive 102.

Axial displacement of the drive chain 104 is preferably limited, such that it does not yield or deform readily in response to axial forces. As used herein, the term "axial" means extending in a direction that is generally parallel to the longitudinal axis A and the outer surface S of a substantially cylindrical structure that is to be inspected.

Preferably, any significant axial displacement that would otherwise occur, due for example to slippage of or to the tolerance between each roller 108 and the associated drive chain link 106, is substantially prevented by connecting the carriage 100, via a substantially rigid coupling 118 and wheels 120, to a guide track 122. The coupling 118 and wheels 120 restrict relative axial displacement of the carriage 100 with respect to the guide track 122. It should be noted that axial force, displacement, velocity, and acceleration may include vector components that are parallel to either or both the longitudinal axis A and the surface S.

More specifically, the guide track assembly 30 includes the coupling 118, the guide track 122, and means for rotatably engaging the guide track 122, such as at least one wheel 120. The exemplary guide track 122 includes a series of interconnected links 124, and is wrapped around to securely engage the outer surface S of the conduit 20. The drive chain 104 is sufficiently flexible radially to conform to the curvature of a conduit 20. The term "radial" means extending outward from the longitudinal axis A and toward the surface S, including extending perpendicularly with respect to either or both the longitudinal axis A and the surface S. Once wrapped around the conduit 20, the guide track 122 remains fixed in place as the carriage 100 and drive chain 104 rotate around the conduit 20, when driven by the circumferential drive 102 (FIG. 3). Close association between the wheels 120 and the guide track 122 can be maintained using an optional load-sensitive spring-loaded junction 130 between the coupling 118 and a wheel housing 128, which presses the wheels 120 toward the guide track and the outer surface S of the conduit 20. As used herein, the term "spring-loaded junction" refers to any expandable connection expansion of which is driven by means of spring tension, hydraulics, pneumatics or other applications of pressure or compression. Fine tuning of the association between the coupling 118, wheel housing 128, spring-loaded junction 130 and guide track 122 can be accomplished via adjusting mechanism 131, which includes a thumbscrew or other means for increasing the compression of the spring-loaded connection 130.

Further, it is contemplated that in certain embodiments, the drive chain 104 may be radially expandable, while maintaining its relative axial inelasticity, such that the drive chain 104 can expand in radius to conform to pipes of various sizes. Radial expansion may be accomplished by adding, removing, adjusting or replacing links in the drive chain 104, as will be described in more detail below. The number of links 106 required to fit around the circumference of the conduit 20 is procedurally controlled, such as by consulting a table listing the circumference range and the number of links required for each size. A tensioning mechanism is used to secure the drive chain to the outer surface S of the conduit 20, which in the exemplary embodiment includes a ratchet strap 107. Alternatively, in certain embodiments, radial expansion can be achieved with a drive chain 104 the length of which can be incrementally adjusted by adding or removing links 106 or using adjustable sized links (not shown).

Like the drive chain 104, the guide track 122 is preferably inelastic axially, such that it does not yield or deform in response to axial forces. The guide track 122 is sufficiently flexible radially to conform to the curvature of the cylindrical conduit 20. Further, it is contemplated that in certain embodiments, the guide track 122 may be radially expandable, while maintaining its axial inelasticity, such that the guide track 122 can expand in radius to conform to pipes of various sizes. Radial expansion may be accomplished by adding, removing, adjusting or replacing links in the guide track 122, as will be described in more detail below, to size the guide track 122 according to the diameter of the cylindrical conduit 20. The number of links required for the guide track may be controlled procedurally by a table listing pipe circumference ranges versus the number of guide track links required. In certain embodiments, a tensioning link 126 is used to securely fasten the guide track 122 to the outer surface S of the conduit 20. Radial expansion can be achieved by incrementally adjusting the tensioning link 126 to tighten or loosen the guide track 122 to achieve very close conformity to and non-slip engagement with the cylindrical conduit 20. For example, the tensioning link 126 includes a threaded connection that can be tightened or loosened to incrementally adjust the closeness of the fit between the guide track 122 and the conduit 20.

In certain embodiments, compressible feet (not shown) made of a slip-resistant material, such as rubber, are disposed between the guide track 122 and the conduit 20 to further fix the position of the guide track 122 and prevent slippage. As the guide track 122 is adjusted to fit tightly around the conduit 20, the feet are compressed between the two. This close fit fixes the position of the guide track 122, which prevents drift of the carriage 100 in use with horizontal, vertical and diagonally positioned conduits 20.

The frame 116 of the carriage 100 is fitted with rollers 109 that cooperate with the drive chain rollers 108 to transport the carriage 100 around the conduit 20. To mitigate rotational friction, the rollers 108, 109 facilitate transmission of rotational motion R generated by the circumferential drive 102 to the carriage 100, thereby enabling the transducer 110 to access the entire circumference of a cylindrical conduit 20. Translational motion T of the transducer 110 can be achieved manually, or by automatically adjusting the axial position of the transducer 110 using the axial drive 112, e.g., a linear actuator. Rotational motion R of the transducer can be achieved manually or automatically by operation of the circumferential drive 102. The drive chain 104 can be connected to the carriage 100 at any point along a drive bar 142. The circumferential drive 102 includes a transmission 146, such as a belt or chain drive, that drives around the circumference of the conduit 20, and thereby transports the carriage 100 along the same path, with undesirable axial movement restricted by the guide track 122, and intended axial translation provided by the axial drive 112. By these means, the transducer 110 can be transported over the entirety of a selected region of the cylindrical conduit 20 in a controlled fashion.

The transducer 110 is transported axially along a set of lower linear journals 113 and upper linear journals 114. The journals 113, 114 are substantially linear shafts that extend longitudinally between opposite ends of the frame 116 of the carriage 100. The transducer 110 is mounted in a transducer housing 132 that includes a port 133 in which the transducer is seated so as to contact or be placed in optimal proximity with respect to the outer surface S of the conduit 20. The transducer housing 132 is carried between bearing brackets 134 that travel directly on the journals 113, 114. To reduce friction between the journals 113, 114 and the bearing brackets 134, the bearing brackets 134 may include circular bearings 135 that encircle the journals 113, 114. To drive the bearing brackets 134 along journals 113, 114, the axial drive 112 connected to the bearing brackets 134 includes a motor 136. The carriage 100 includes a toothed rack 138 and the motor 136 drives a pinion gear 140 that communicates with the rack 138 to provide axial translation T. Those skilled in the art will readily appreciate that alternative means for generating axial displacement may be used, such as but not limited to hydraulics, or a worm gear assembly. The journals 113, 114 maintain alignment of the bearing brackets 134 and transducer housing 132 through the axial range of motion.

Another beneficial feature of the various embodiments is the gimbaling arrangement for the transducer 110. The gimbaling arrangement is spring-loaded so that a constant downward force is applied to maintain contact or optimal proximity between the transducer 110 and the outer surface S of the conduit 20 that is being examined. In certain embodiments, this accomplished by means of a spring 148 attached to suspension 150, which can be an internal component of each bracket 134. Alternatively, the spring 148 may be permanently or detachably connected to the outside of the bracket 134, where the spring 148 would connect a fixed element of the frame 116 to a floating element (such as the suspension 150) to constantly pull down on the transducer housing 132. In lieu of or in addition to a spring 148, the suspension 150 may include any mechanism that generates a load-sensitive downward force that is driven, for example by means of hydraulics, pneumatics, spring tension or other pressure or compression forces. In other embodiments, the suspension is a component of the transducer housing 132 itself rather than the bracket 134. The close association between the drive chain 104 and the conduit, coupled with the spring-loaded gimbaling, ensure optimal contact or proximity between the transducer 110 and the outer surface S of the conduit 20.

Referring now to FIG. 4, which is a functional diagram, it can be seen that the various embodiments of the invention are particularly useful in connection with conduit that is tapered. As used herein, the term "tapered" refers to conduit or a section thereof that has a diameter at one end that is greater than the diameter at another end, so as to define a taper angle α. The drive chain 104 and the guide track 122 are spaced apart from one another by a distance X, which is less than the length L of the conduit 20. Specifically, this separation advantageously allows the diameter D1 of the drive chain 104 to be greater or less than the diameter D2 of the guide track 122, which in turn enables close conformity to a conduit 20 that is tapered. The embodiments of the present invention have been found to perform well with a taper angle α of 5%, which is greater than the 3% reactor pipe taper that is currently allowable under U.S. regulations, although it is anticipated to perform well at a variety of other taper angles.

With tapered conduit, prior art scanning instruments are typically installed toward the smaller diameter end ("pipe end" 24) of the conduit, and axial translation is achieved by extending toward the larger diameter end ("nozzle end" 22) an arm on which a transducer is mounted. In contrast, the carriage 100 can be installed on either end, as it is completely reversible according to the available clearance or other environmental, ergonomic or situational factors and circumstances. Thus, the present invention allows an operator to customize any installation to provide maximum coverage area for the inspection.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasonic scanning apparatus for inspecting a circumferential section of conduit, comprising:
    a carriage, comprising:
        a frame configured to be mounted directly on the surface of the conduit and to rotate around the circumference of the conduit; and
        at least one linear journal extending between opposed ends of the frame;
    a transducer configured to travel axially along the at least one linear journal;
    a circumferential drive configured to generate rotational motion of the carriage around the circumference of the conduit; and
    a guide track that is configured to be fixedly secured adjacent to the circumferential section of conduit so as to prevent axial drift of the carriage.

2. The ultrasonic scanning apparatus of claim 1, further comprising a drive chain configured to hold the carriage in close association to the conduit and to translate to the carriage rotational motion generated by the circumferential drive.

3. The ultrasonic scanning apparatus of claim 1, further comprising a coupling for defining a substantially axially rigid connection between the carriage and the guide track.

4. The ultrasonic scanning apparatus of claim 3, further comprising a wheel for engaging the guide track.

5. The ultrasonic scanning apparatus of claim 4, further comprising a spring-loaded junction connected to the coupling, the spring-loaded junction generating a downward force on the wheel to maintain contact with the guide track.

6. The ultrasonic scanning apparatus of claim 1, further comprising:
    a transducer housing for carrying the transducer; and
    a bearing bracket slidably attached to at least one linear journal and to the transducer housing;
    wherein the bearing bracket includes a spring-loaded suspension that generates a downward force on the transducer housing so as to maintain a preselected proximity between the transducer and the conduit.

7. The ultrasonic scanning apparatus of claim 6, wherein the spring-loaded suspension is load sensitive to maintain the preselected proximity substantially consistently at any point on the circumference of the conduit.

8. The ultrasonic scanning apparatus of claim 1, further comprising:
    a transducer housing for carrying the transducer; and
    a bearing bracket slidably attached to at least one linear journal and to the transducer housing;
    wherein the transducer housing includes a spring-loaded suspension that generates a downward force on the transducer so as to maintain a preselected proximity between the transducer and the conduit.

9. The ultrasonic scanning apparatus of claim 8, wherein the spring-loaded suspension is load sensitive to maintain the preselected proximity substantially consistently at any point on the circumference of the conduit.

10. The ultrasonic scanning apparatus of claim 1, further comprising a drive chain that is configured to connect the circumferential drive to the carriage and to hold the carriage in close contact with the outer surface of the conduit;
    wherein the drive chain is spaced apart from the guide track.

11. The ultrasonic scanning apparatus of claim 1, further comprising an axial drive for providing axial translation of the transducer along the at least one linear journal.

12. The ultrasonic scanning apparatus of claim 10, wherein:
    the axial drive comprises a drive motor and a pinion gear;
    the carriage comprises a rack configured to engage the pinion gear; and
    the drive motor is configured to drive the pinion gear along the rack to propel the transducer along the at least one linear journal.

13. A guide track assembly for preventing axial drift of an ultrasonic scanning apparatus that is mounted directly on a circumferential section of conduit, comprising:
    a guide track that is configured to be fixedly secured adjacent to the circumferential section of conduit; and
    a coupling for defining a substantially axially rigid connection between the ultrasonic scanning apparatus and the guide track;
    wherein the guide track is configured to be spaced apart from the ultrasonic scanning apparatus.

14. The guide track assembly of claim 13, further comprising a wheel for engaging the guide track.

15. The guide track assembly of claim 14, further comprising a spring-loaded junction connected to the coupling, the spring-loaded junction generating a downward force on the wheel to maintain contact with the guide track.

16. A method for preventing axial drift of an ultrasonic scanning apparatus while inspecting a circumferential section of conduit, comprising:
    fixedly extending a guide track around the section of conduit;
    placing the ultrasonic scanning apparatus directly on the surface of the conduit;

rotatably mounting the ultrasonic scanning apparatus by extending a rotatable drive chain around the section of conduit and by spacing the drive chain apart from the guide track;

coupling the guide track and the ultrasonic scanning apparatus such that the guide track is configured to substantially prevent axial drift of the ultrasonic scanning apparatus during rotation of the ultrasonic scanning apparatus around the conduit.

17. The method of claim 16, further comprising connecting a circumferential drive to the drive chain for providing rotational motion to the ultrasonic scanning apparatus.

18. The method of claim 16, wherein coupling the guide track and the ultrasonic scanning apparatus comprises providing a substantially axially rigid connection between the guide track and the ultrasonic scanning apparatus.

19. The ultrasonic scanning apparatus of claim 2, wherein a diameter D1 of the drive chain is unequal to a diameter D2 of the guide track.

20. The ultrasonic scanning apparatus of claim 5, wherein the spring-loaded junction further generates the downward force on the wheel to press the wheel toward the surface of the conduit.

* * * * *